United States Patent [19]
Delhaye et al.

[11] Patent Number: 4,678,277
[45] Date of Patent: Jul. 7, 1987

[54] METHOD OF DISCRIMINATION IN SPECTROMETRY

[76] Inventors: Michel Delhaye, 80, rue Thiers;
André Deffontaine, 39, rue Degas;
André Chapput, 78, rue Faidherbe, all of 59650 Villeneuve d'Ascq;
Michel Bridoux, 1, rue Jean Mermoz, 59890 Quesnoy sur Deule; Edouard Da Silva, Place de l'Eglise, 60390 Auneuil, all of France

[21] Appl. No.: 655,024

[22] Filed: Sep. 26, 1984

[30] Foreign Application Priority Data

Sep. 30, 1983 [FR] France ............................ 83 15939

[51] Int. Cl.$^4$ .......................... G01J 3/44; G01N 21/65
[52] U.S. Cl. .................................................. 356/301
[58] Field of Search ........................ 356/301, 352, 346

[56] References Cited

U.S. PATENT DOCUMENTS 3,984,190  10/1976  Barrett et al. ...................... 356/301
3,999,854  12/1976  Barrett ............................ 356/301
4,005,937  2/1977   Barrett ............................ 356/301

FOREIGN PATENT DOCUMENTS 2212498  3/1972  Fed. Rep. of Germany ...... 356/301

OTHER PUBLICATIONS

Proffitt et al., *Applied Optics*, vol. 10, No. 3, Mar. 1971, pp. 531–534.

*Primary Examiner*—F. L. Evans
*Attorney, Agent, or Firm*—Robert E. Burns; Emmanuel J. Lobato; Bruce L. Adams

[57] ABSTRACT

The invention relates to a method of discrimination in spectrometry, particularly of eliminating phenomena of fluorescence in Raman spectrometry. According to the invention, a sample (6) is excited by a luminous pulse (5) generated from a laser (1). The light (7) emitted by the sample (6) is directed into an interferometer (8) of which the duration of a round trip of a luminous ray is significantly longer than the duration of the pulse of the incident wave and shorter than the duration of the phenomenon of fluorescence. The resulting light (9) is then directed to a second interferometer (10) of which the optical path is slightly different from that of the preceding interferometer (8). The light (11) is recovered at the outlet of the second interferometer (10) and this wave is analyzed by means of a spectrometer (12). The invention is applicable particularly to the analyzing of samples in the chemical industry.

10 Claims, 10 Drawing Figures

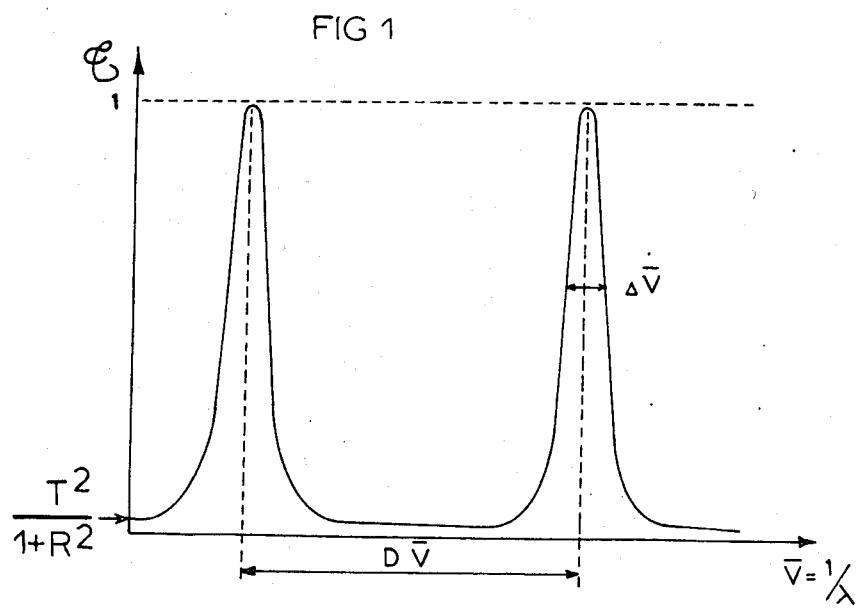
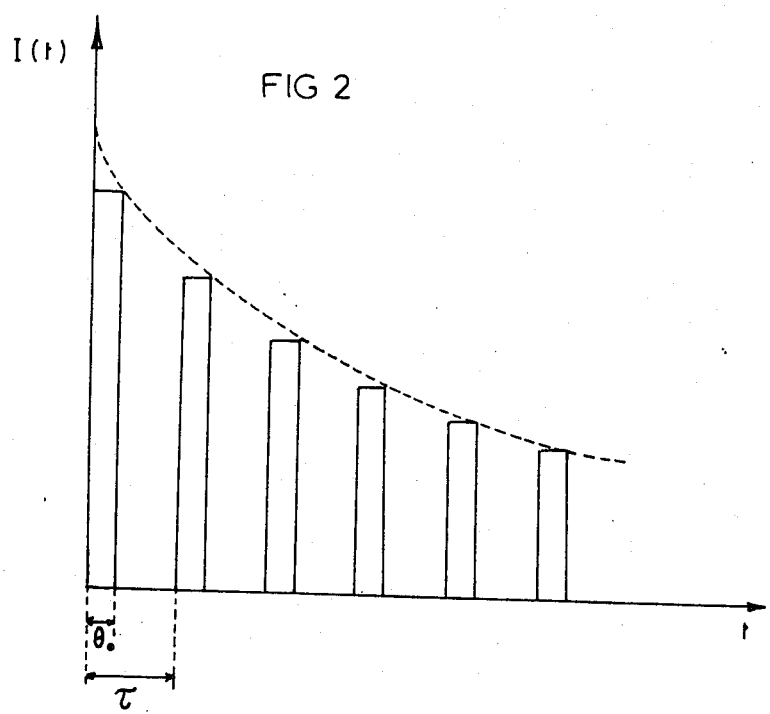

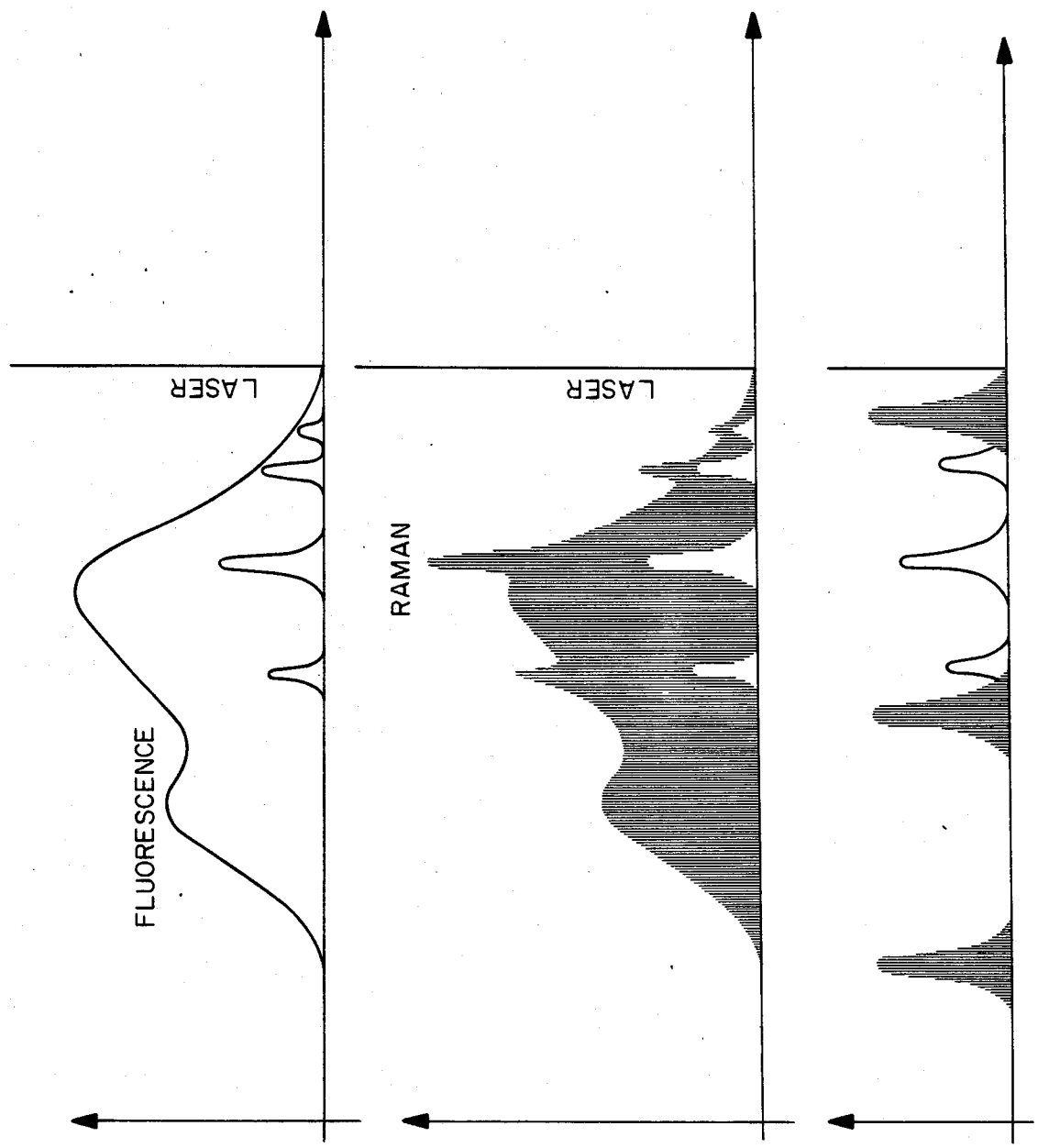

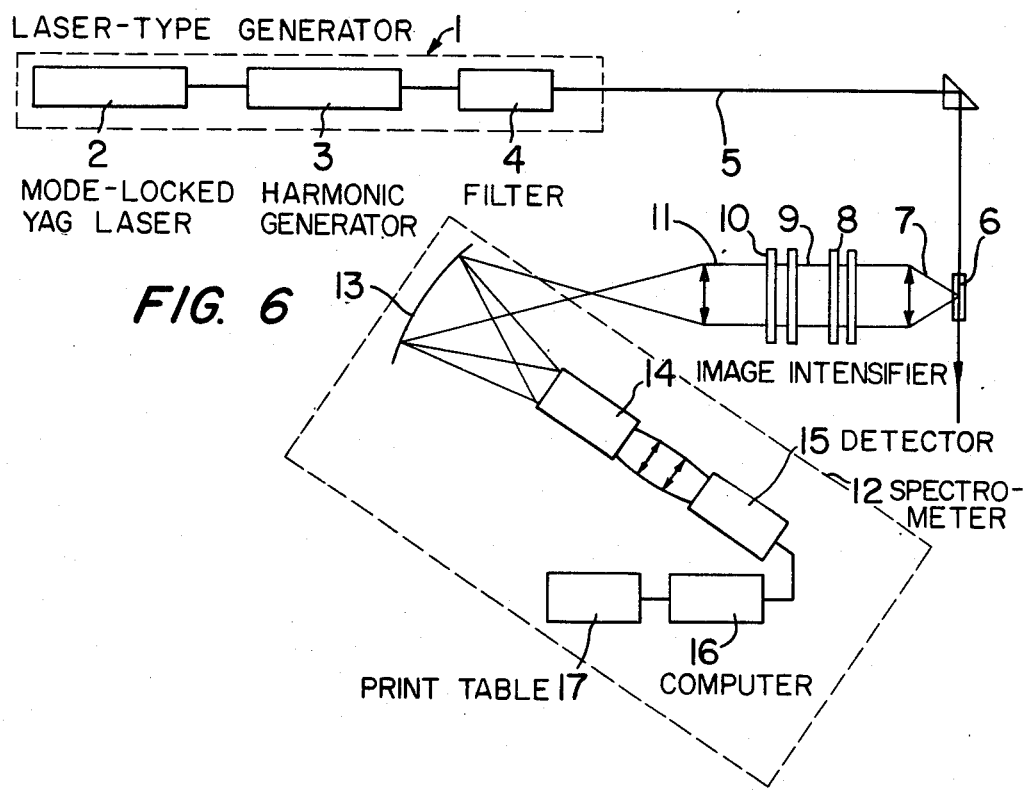
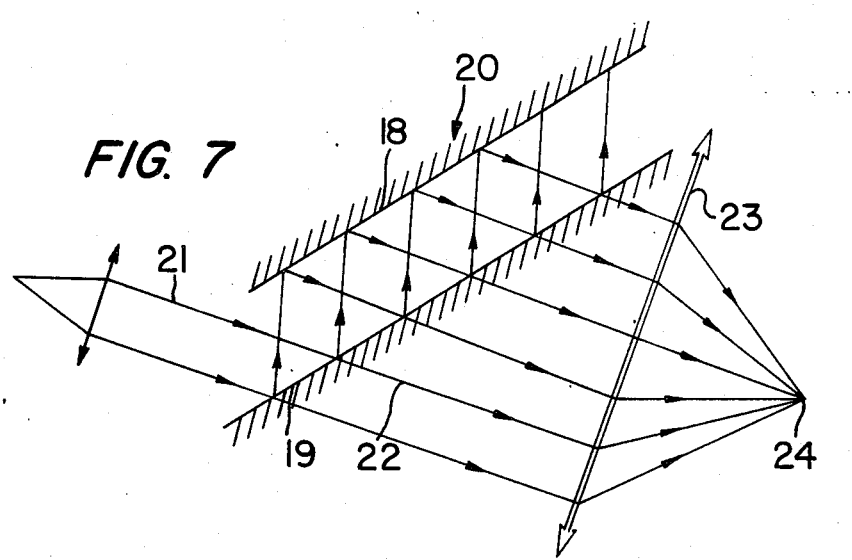

METHOD OF DISCRIMINATION IN SPECTROMETRY

BACKGROUND OF THE INVENTION

The invention relates to a method of discrimination in spectrometry as well as to a device for implementing the method. The invention will be applicable particularly to Raman spectrometry for analysing samples, notably in the chemical industry.

At present, the analysis of samples in Raman spectrometry is a difficult operation in some cases.

As a matter of fact, the presence of fluorescent impurities in the samples is the main cause for failure in Raman spectrometry. In spite of any technical progress achieved that allowed for increasing sensitivity and in spite of the data processing of the signals that improves the signal-to-noise ratio, the detection of low intensity Raman lines can become quite difficult if they are superposed on a continuous high intensity background as encountered in phenomena of fluorescence.

The photoelectric detectors used in the visible close ultraviolet or very close infrared range have a high quantum gain and feature a very low dark current so that the predominant source of noise consists of what is generally known as "photon noise". Under these conditions, the presence of a wide spectral band of fluorescence in the spectral region where the Raman spectrum has to be observed, is the cause of significant fluctuations in photoelectric detection.

Most of the techniques proposed to remedy this situation such as frequency modulation or the subtraction of continuous background are ineffective where the "photon noise" is concerned.

At present, the only physically valid solution consists in eliminating most of the light emitted by fluorescence by using a spectroscopy technique resolved in time. This temporal discrimination technique requires the use of electronic or electrooptical picosecond "doors". Unfortunately, it is impossible to materialize them at reasonable cost and, consequently, to consider their development in the industry.

SUMMARY OF THE INVENTION

It is the primary object of this invention to provide a method for temporal discrimination in spectrometry that can be used for industrial purposes. Meaning that it uses reliable apparatus and that the costs involved are quite reasonable.

According to the method of discrimination of this invention, the elimination of the phenomena of fluorescence is carried out in a static manner that provides great reliability and eliminates the need of using equipments with very short response times.

Other objects and advantages of this invention will appear as the following description proceeds which is given, however, by way of illustration and not of limitation.

The method of discrimination in spectrometry, particularly of eliminating fluorescence in Raman spectrometry for analysing samples by investigating the features of the light emitted by the sample, is characterized in that:

a luminous pulse is directed to the sample, which pulse is generated, in particular, by a laser;

the light emitted by the sample is directed to an interferometer of which a duration of a round trip of a luminous ray is significantly longer than the duration of the incident pulse emitted and shorter than the duration of the phenomenon of fluorescence;

the light is collected at the interferometer outlet and the wave is analysed by means of a measuring instrument e.g. of a spectrometer-type instrument.

The device of discrimination in spectrometry, particularly for eliminating fluorescence in Raman spectrometry according to the implementation of the method of this invention, is characterized by the fact that it is formed of:

one luminous pulse generator (typical duration $10^{-9}$ to $10^{-12}$ second), e.g. a laser-type generator set up in such a manner as to direct the luminous pulse on the sample;

one interferometer that collects the light emitted by the sample of which the duration of a round trip is significantly longer than the duration of the pulse of the incident wave and shorter than the duration of the phenomenon of fluorescense;

one second interferometer of which the optical path is slightly different from that of the first interferometer;

one spectral analysis equipment.

THE DRAWINGS

FIG. 1 illustrates the transmission curve of a multiple wave interferometer as a function of the wave number.

FIG. 2 illustrates the temporal response curve of a Fabry-Perot-type interferometer with one rectangular pulse of a duration $\theta$ shorter than the time $\tau$ that is correspondent to the round trip duration.

FIG. 5a illustrates the shape of the spectra resulting from fluorescence and from the Raman effect.

FIG. 5b illustrates the shape of the spectra of FIG. 5a subsequent to passage through an interferometer.

FIG. 5c illustrates the shape of the spectra resulting from FIG. 5b subsequent to passage through a second interferometer.

FIG. 6 shows diagrammatically a device for implementing the method of this invention.

FIG. 7 illustrates a preferred embodiment of an interferometer according to the invention.

DESCRIPTION OF THE PREFERRED EMBODIMENTS

Figure 3:
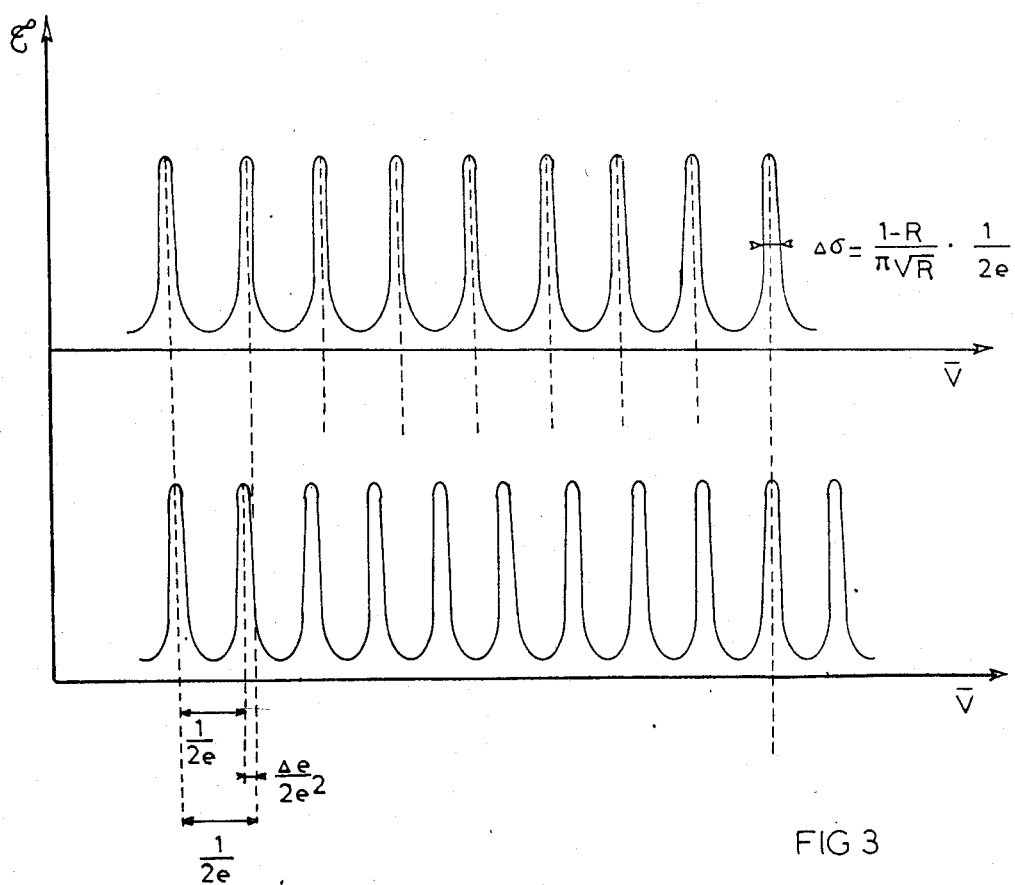
FIG. 3 illustrates the transmission curves of two Fabry-Perot-type interferometers of which the optical paths are slightly different.

The analysis of materials by applying the Raman effect provides the advantage of being non-destructive. The results allow for obtaining a both qualitative and quantitative determination of the various elements of which a sample is composed.

The Raman effect is characteristic of the molecular vibrations of the sample components and reveals itself by an emission of waves of different frequencies emitted when the sample is being excited, notably by means of a luminous pulse.

One of the features of the Raman effect is, in particular, its duration quite similar to that of the exciting pulse when the latter is in the range of a few picoseconds.

Unfortunately generally when the samples are fluorescent or contain fluorescent impurities, jointly with the Raman effect will appear phenomena of fluorescence characterized in that they feature a spectrum of great width and an amplitude clearly greater than that of the waves resulting from the Raman effect.

Furthermore, the phenomena of fluorescence have a duration significantly longer than that of the Raman effect since it attains typically $10^{-9}$ second or more.

Because the Raman effect reveals itself by a frequency shift of the wave emitted as compared to the incident wave, we may attempt to discriminate the waves originating from the fluorescence as compared to the Raman effect by selecting an incident radiation wavelength relatively remote from the wavelengths generated by the phenomenon of fluorescence.

Unfortunately, for technical reasons, it is not always possible to select freely the wavelength of the exciting pulse.

As the wave emitted by the Raman effect starts simultaneously with the incident wave whereas the phenomena of fluorescence are somewhat delayed, it is possible to consider a temporal discrimination while taking into account only the very first moments of the wave emitted by the sample, i.e. a few picoseconds. Unfortunately, the obturating devices featuring a response time of a few picoseconds are extremely difficult to handle and their cost price excludes any industrial application.

The method of discrimination, according to this invention, in spectrometry is static. According to this method, it is possible to eliminate the influence of the phenomena of fluorescence in Raman spectrometry in order to show up the waves originating from the Raman effect.

The method according to this invention is designed particularly for industrial application as it uses reliable components at a reasonable cost price.

The principle of the method according to this invention allows for treating long pulses differently as compared to short pulses.

As emissions of fluorescence are considered as long pulses compared to the waves emitted by the Raman effect which are of short duration, we may, according to the method of this invention, attenuate the amplitude of the waves originating from the fluorescence without attenuating the amplitude of the waves originating from the Raman effect, which allows for observing, subsequent to this treatment, the Raman spectrum.

In order to apply the method of discrimination according to this invention, it is first of all necessary to excite the sample by means of a luminous pulse. The duration of this luminous pulse will have to be significantly shorter than the typical durations of the phenomena of fluorescence i.e. of a few nanoseconds. The excitation of the sample will have to be achieved by means of a luminous pulse with a duration of a few picoseconds.

The sample excited in this manner will first emit by the Raman effect a radiation quite similar in duration to that of the pulse exciting of a few picoseconds and emit a radiation, due to fluorescence, of a duration of a few nanoseconds or more.

According to the method of the invention, the luminous pulse exciting the sample will be generated, preferably, from a pulse laser.

The light emitted by the energized sample is directed into an interferometer i.e. any apparatus in which two or more waves are made to interfere. The type of interferometer selected does not matter but in view of providing a better understanding of the invention, the description involves a Fabry-Perot-type interferometer.

This is an apparatus composed of two semi-reflecting plane mirrors arranged parallel one of the other at a low distance.

Electromagnetic waves penetrating into the interferometer will be reflected partially by the mirrors of which it is made. Phenomena of interference will arise for these waves and at the outlet of the interferometer, only the waves with certain frequencies will be preserved.

FIG. 1 illustrates the transmission curve of a Fabry-Perot-type interferometer.

By assuming that the spectrum of the wave incident on the interferometer is a unitary amplitude spectrum, we may observe in FIG. 1 the spectrum of the wave at the interferometer outlet. The curve of FIG. 1 illustrates the amplitude of the wave at the interferometer outlet as a function of the wave number.

In the case of a Fabry-Perot-type interferometer, the coefficient of transmission $\theta$ is given by the formula below:

$$\tau = \frac{1}{1 + \frac{4R}{(1-R)} 2 \sin^2 \frac{\phi}{2}}$$

where R is the coefficient of reflection of the semi-reflecting mirrors and $\phi$ the phase difference between the various interfering waves.

$\phi = 4\pi e \nu = 2\pi p$ for a radiation perpendicular to the surface of the mirrors. e, $\nu$, p indicate, respectively, the distance that separates the parallel mirrors, the wave number and the order of interference.

We could consider an interferometer where the waves are propagating in an environment a medium of index n, in which case the optical path would depend on this index.

When the optical path 2e, for a Fabry-Perot-type interferometer, has been determined and when the incident light is white light, the maximum coefficient of transmission is obtained for the waves verifying the relation:

$$D\bar{\nu} = \frac{1}{2e}$$

where $D\nu$ is known as the free spectral range. The ratio of the free spectral range to and the width at half maximum of the interference fringes determines the theoretical finesse of the interferometer:

$$F = \frac{D\bar{\nu}}{\Delta \nu} = \frac{\pi \sqrt{R}}{1 - R}$$

FIG. 1 shows the various elements characterizing a Fabry-Perot-type interferometer where we find $D\nu$ and $\Delta\nu$.

Because of its principle, an interferometer will function according to the method described earlier only to the extent where it is possible to establish a stationary regime in the space that separates the mirrors of the interferometer.

The conventional theory of the interferometer may therefore not be applied when it is illuminated by a luminous pulse of very short duration.

If we designate by $\tau$ the duration of the round trip of a luminous ray between the mirrors of an interferometer, we obtain in the case of a normal incidence $$\tau = \frac{2e}{C}$$

where C is the speed of light and 2e represents the optical path in a medium where the index is equal to 1.

If the duration of a luminous pulse $(\theta_o)$ is less than $\tau$, the Fabry-Perot interferometer will transmit a succession of pulses, each of $\theta_o$ duration. The train of waves wherein the waves follow one another in a discontinuous succession with a pseudoperiod $\tau$, is as illustrated by FIG. 2.

The interferometer divides the incident wave and transmits it at regular intervals; to note, however, that except for the losses through absorption, all of the energy passes through the interferometer, either by reflection or by transmission, contrary to its conventional use.

On the other hand, if the pulse duration $\theta_o$ is greater than $\tau$, phenomena of interference will occur in the interferometer and in this case, this causes changes in the shape, duration and spectral distribution of the energy of the pulse passing through.

Now if the interferometer is illuminated simultaneously by two pulses with durations, respectively, shorter and longer as compared to the optical course time $\tau$ of the interferometer, the study above shows that the first pulse passes through the interferometer without suffering any interference, contrary to the second pulse that is "spectrally filtered" by the interferometer. The method according to this invention thus allows for distinguishing between the two pulses.

If, for instance, the first pulse $(\theta_1)$ consists of a Raman spectrum excited by the pulsed laser of 25 picoseconds duration, it is known that Raman effect will occur during a very short time similar to the duration of the excitation. The second pulse will originate from the spectrum of fluorescence, the duration of which is significantly longer than $\theta_1$ (typically $\theta_2 = 10^{-9} - 10^{-8}$ second).

For a mirror separation e=5 mm between the mirrors of a Fabry-Perot interferometer, $\tau = 33$ picoseconds i.e. $\theta_1 < \tau$; therefrom results that the Raman lines fail to cause any interference but as $\theta_2 > \tau$, the transmission of the waves of fluorescence through the interferometer causes an attenuation as illustrated by FIG. 1. The fluorescence features the shape of a notched spectrum Edser-Butler Bands that can be observed in the focal plane of a spectrometer.

According to the method of this invention, it is thus possible to observe the lines due to the Raman effect in the free spectral windows between the peaks resulting from the notched spectrum due to the wave of fluorescence that has passed through the interferometer.

It is established, however, in practice that the transmitted bands of the spectrum of fluorescence are extremely fine.

FIG. 5a illustrates the intensity of the phenomenon of fluorescence as a function of the number of waves as well as the intensity of the lines of the Raman effect.

FIG. 5b illustrates the spectrum resulting after the passage through the Fabry-Perot-type interferometer.

The transmitted peaks of the spectrum of fluorescence show to be clearly finer as compared to the width of the Raman lines which explains the almost total impossibility of detecting the presence of Raman lines among the peaks of the spectrum of fluorescence.

To solve this problem we use according to the method of this invention a second interferometer installed in series with the first one. We could also use the same interferometer by having the luminous wave pass again through this one with an optical path slightly different from that used previously.

It is not possible, as a matter of fact, to increase significantly the free spectral range between the peaks of the resulting spectrum, notably by reducing the distance separating the mirrors as the first consequential effect of this would be to shorten the optical round trip duration $\tau$ that could become shorter then $\theta_1$.

Therefore we use, according to the method of this invention, a second interferometer installed in series with the first one, the mirror separation of which is e' slightly different from e.

The transmission curves of the two interferometers with close but different separations are illustrated by FIG. 3.

Supposing, for the purpose of simplifying calculations, that the coefficients of reflection of the mirrors of the two interferometers are identical, we can demonstrate that the distance separating the fringes of the two interferometers is equal to $$\frac{\Delta e}{2e^2} \ (\Delta e = e' - e)$$

There is coincidence between the fringes of the two interferometers according to a step p such as:

$$p \frac{\Delta e}{2e^2} = \frac{1}{2e} \text{ i.e. } p = \frac{e}{\Delta e}$$

The fringes are characterized by their width at half maximum $$\Delta \sigma = \frac{1 - R}{2\pi e \sqrt{R}}$$

and for each coincidence, the interference fringes are superposed.

Figure 4:
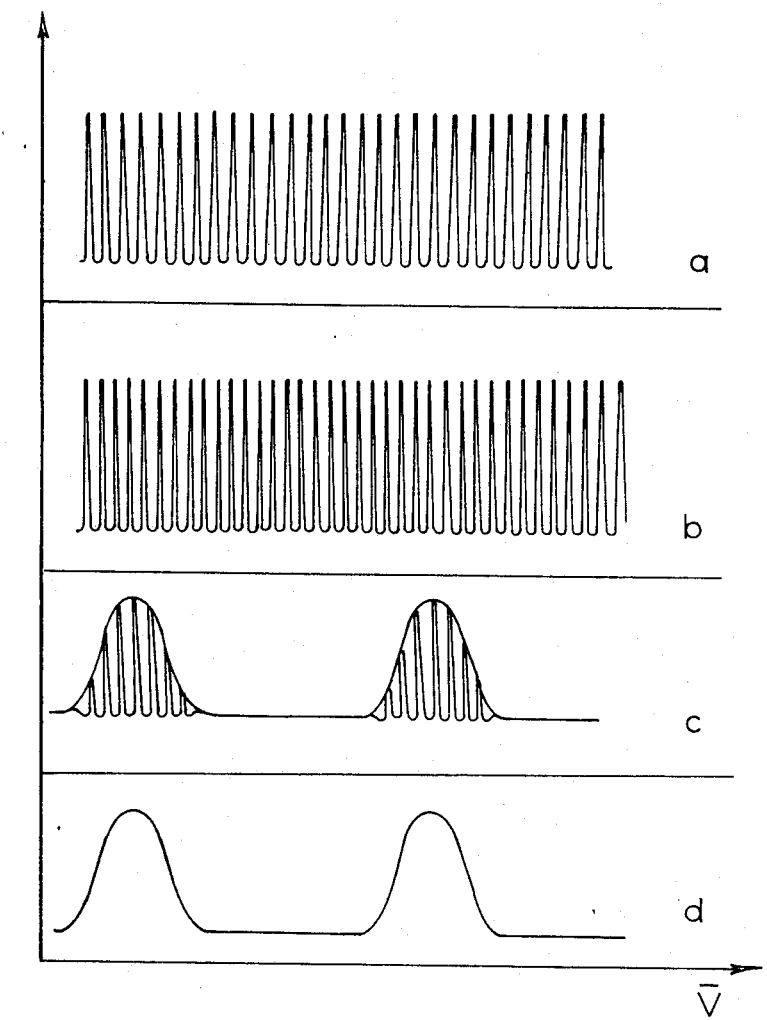
FIG. 4a illustrates the transmission curve of an interferometer of which the optical path has a length e.
FIG. 4b illustrates the transmission curve of an interferometer of which the optical path has a length $e + \Delta e$.
FIG. 4c illustrates the amplitude curve of a light that has passed through the two interferometers of FIGS. 4a and 4b.
FIG. 4d illustrates the envelope of FIG. 4c.

FIG. 4a illustrates the spectrum of a white light that has passed through a first interferometer.

FIG. 4b illustrates the spectrum of a white light that has passed through an interferometer, the separation of which is slightly different from that of the spectrometer of FIG. 4a.

FIG. 4c illustrates the spectrum of a white light that has passed, successively, through the interferometers of the FIGS. 4a and 4b. We can observe the presence of the superposition fringes, the distance of which is clearly larger than the distance separating the peaks of the spectrum.

As the resolution of the spectrometers is quite smaller than that of the interferometers, FIG. 4d illustrates the envelope resulting from FIG. 4c such as it can be observed with a spectrograph.

In a first rough estimate, the number of superposition fringes (k) may be estimated by applying the formula below:

$$\frac{k}{2} \cdot \frac{\Delta e}{2e^2} = \frac{1-R}{2\pi e \sqrt{R}}$$

$$k = \frac{2(1-R)e}{\pi \sqrt{R} \, \Delta 2}$$

To note that the ratio:

$$\frac{P}{k} = \frac{\pi \sqrt{R}}{2(1-R)}$$

does not depend on e and e. It is only a function of R. This ratio may serve to define the finesse of a coupling of two interferometers.

For e=5 mm, e'=5.02 mm and R=0.9 for each mirror, the free spectral range is $D\nu=250$ cm$^{-1}$ and $P/k=15$. This makes possible the observation of the Raman spectrum in the free spectral windows while the spectrum of fluorescence is greatly attenuated.

FIG. 5c illustrates the spectrum obtained after passage in two interferometers. We can observe the presence of the Raman spectrum in the windows separating the superposition fringes from the spectrum of fluorescence.

According to the method of this invention it is thus possible to attenuate very greatly the intensity of the spectrum due to fluorescence without changing the intensity of the Raman spectrum.

In addition, by changing the optical path of the interferometers in synchronization with the scanning of the spectrometer, it is possible to scan the spectrum and to observe the whole of the Raman spectrum in the windows separating the supersposition fringes.

Up to the present time, it was always considered to use a fixed wave number luminous pulsed source, which required for determining the features of the sample, the scanning of the spectrum of the light emitted by the sample over a range covering a significant number of waves range.

We may also consider using a variable wave number luminous pulse source coupled with a spectrometer adjusted to a fixed wave number for analysing the sample.

Lasers with a tunable wave number are perfectly adjusted to this kind of experiment and by having this laser emit successively luminous pulses of different wave numbers, it is possible to record by means of the spectrometer the intensity emitted by the Raman effect for a variable delay between the waves of the incident luminous pulse and the wave number to which the interferometer is adjusted.

FIG. 6 illustrates diagrammatically a device of discrimination for implementing the method described above.

The device is fitted, first of all, with a luminous pulse generator 1, notably a laser-type generator. In particular, the luminous pulse generator 1 comprises a mode-locked YAG laser 2 followed by a harmonic generator 3 that precedes a filter 4. The wave emitted 5 is directed to a sample 6. The luminous waves 7 emitted by the sample 6 are directed to a first interferometer 8, the optical course time of which is equal to $\tau$.

The waves 9 coming from the interferometer 8 is directed into a second interferometer 10, the round trip duration of which is equal to $\tau'$ slightly different from $\tau$.

The waves 11 coming from the second interferometer 10 are focussed to a spectrometer 12 which is itself composed of e.g. one concave grating 13, one image intensifier 14 and one multi-channel detector 15 or one single-channel detector, one computer 16 and one print table 17.

The spectral analyzer 12 allows for providing through the graphical table 17 the envelope of the spectrum emitted by the sample 6 with attenuation of the intensity of the waves resulting from the fluorescence, in the windows separating the superposition fringes.

In all of the description above, it was considered to use multiple beam interferometers i.e. notably the Fabry-Perot interferometer. It is obvious that this is a particular case and that any type of interferometer may be used.

The Michelson-type two-beam interferometers can be used, in particular, without any problem.

The envelope of the spectrum resulting from a white light passing through a two-wave interferometer features a sine-shaped profile.

This feature can be put to good use, notably in searching for the presence of the Raman spectrum lines in the hollow of the sine where the amplitude of the waves of fluorescence is lowest.

We may also apply simultaneously the spectral scanning of the two-beam interferometer and of a spectrometer. It is possible to combine the two scanning features in such a manner that one Raman line is always in the valley of a sine where the amplitude of fluorescence is insignificant, in order to detect thus the Raman line with the best signal-to-noise ratio.

This is applicable to a very large range of wave numbers.

Where multi-wave-type interferometers such as Fabry-Perot interferometers are concerned, we have to underline that these equipments have a major drawback, namely poor transmission. As a matter of fact, because mirrors featuring a relatively large reflective coefficient are used, a large part of the incident wave is reflected and fails to penetrate between the mirrors.

To remedy this drawback, this invention advocates the use of modified Fabry-Perot interferometers according to FIG. 7.

The mirrors 18 and 19 of the interferometer 20 are slightly unwedged. It is thus possible to have the incident waves 21 penetrate between mirrors 18 and 19 without having the waves pass through mirror 18. Consequently, we select a mirror 18 with a reflectivity as close as possible to 100%.

Through multiple reflections between the mirrors 18 and 19, the incident waves 21 will partially pass through the mirror 19. The various rays that passed through the mirror 19 will then be concentrated by a lens 23 into a focal point 24 where they will interfere.

If we consider a luminous beam of square section (side A) incident on the first interferometer, it will be transformed into a side A and NA rectangular section luminous beam after it has passed through this interferometer, N being the number of beams causing interference. This beam of rectangular section will have to enter entirely into the second interferometer, the mirrors of which are adequately sized; it will leave this interferometer in the shape of a side NA square section beam if we suppose that in the second interferometer, this number of interfering beams is also N (e.g. N could reasonably be about 10).

Such a device demands that the mirrors of the first interferometer have a rectangular shape and are unwedged as shown by FIG. 7. The mirrors of the second interferometer are also unwedged.

Figure 8:
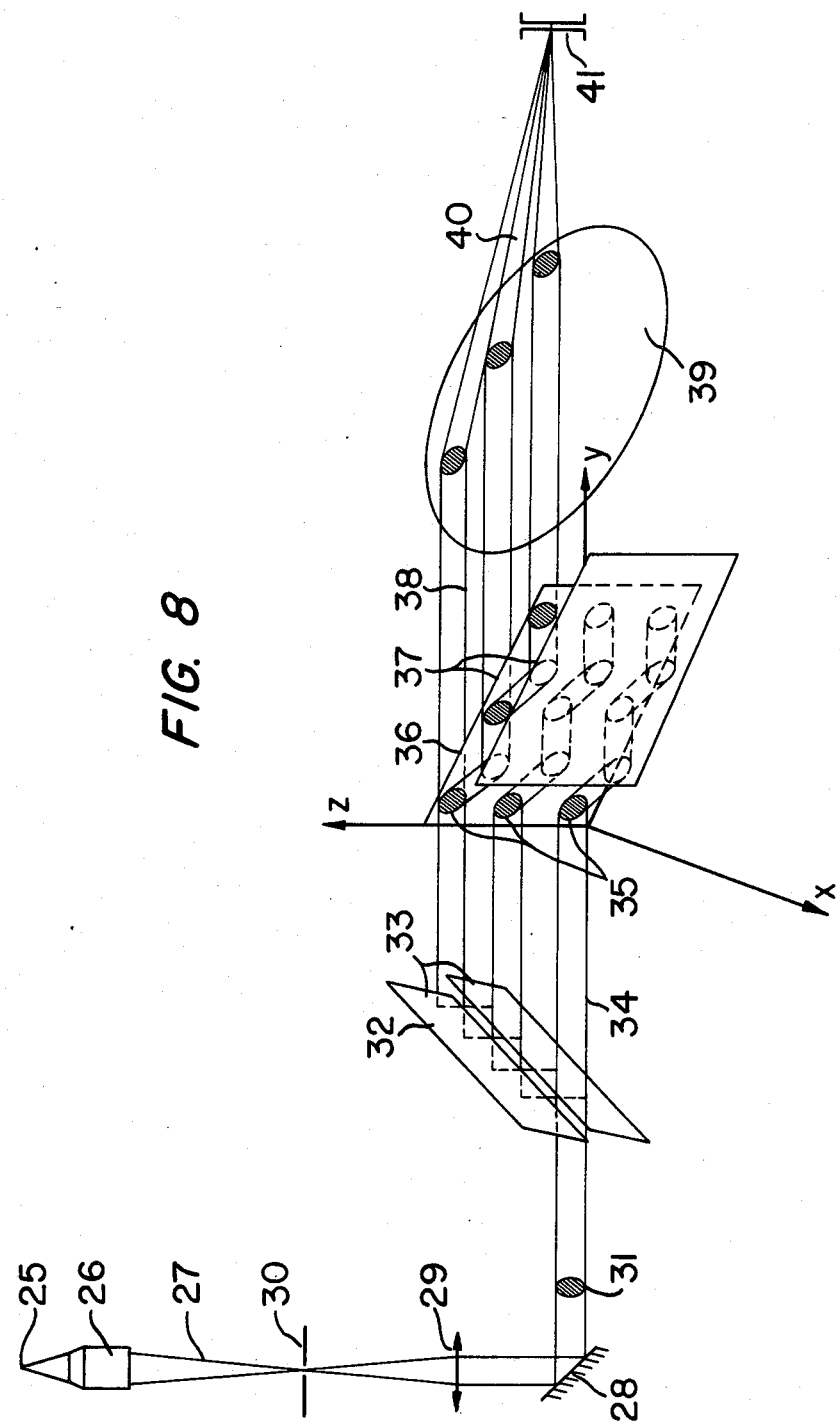
FIG. 8 illustrates a preferred embodiment of two combined interferometers.

FIG. 8 illustrates a preferred embodiment of two combined Fabry-Perot-type interferometers according to the invention.

The luminous waves emitted by the sample 25 are collected, partially at least, by a microscope-type objective 26. The luminous waves 27 are then directed to a mirror 28 preceded by a coupling lens 29 and a diaphragm 30. The return mirror 28 directs the luminous beam 31 to the inlet of a first Fabry-Perot-type interferometer 32 composed of two mirrors 33.

The two mirrors 33 are shifted one as compared to the other as illustrated by FIG. 7 so that the incident beam 31 is able to enter between the mirrors 33 without having first to pass through one of them. By using an Ox, Oy, Oz axis as defined by FIG. 8 i.e. with the Oy axis extending in the direction of the luminous rays 31 and 34, respectively at the inlet and the outlet of the interferometer 32, the Oz axis represents the stretching direction of the beam 31 i.e. the vertical direction of FIG. 8.

As a matter of fact, the interferometer 32 stretches the beam 31 vertically. The stretching plane of the beams is defined as the plane normal to the mirrors 33 of the interferometer 32 and passing through the luminous source, here sample 25 in the case of FIG. 8.

As an example, FIG. 8 shows a vertical stretch of the incident beam 31, according to three beams 35, entering a second interferometer 36, the mirrors 37 of which are orthogonal to the xOy plane defined earlier. This arrangement allows for a stretch of the incident beams 35 according to a direction Ox.

In the example selected for FIG. 8, we also used a spread by the interferometer 26 so as to obtain at the outlet nine beams 38 that are concentrated again by a convergent lens 30 arranged in their path. The beams 40 at the outlet of the lens are then directed to the entrance slit 41 of a spectrometer.

In the example selected we used a stretch so as to have interfere in the first interferometer 32 three beams and, at the outlet of the second interferometer 36, nine waves. In general, this number will be significantly larger and will be increased to about one hundred beams at the outlet of the second interferometer.

As the range of the entering beam is small, this device will provide a larger range at the outlet. This adjustment will find an application particularly for the purpose of associating the microscope objective and the interferometer.

The description above has been given for the purpose of indication only and other embodiments of this invention could have been considered for those conversant with the art without departing from the basic principles of the invention.

What is claimed is:

1. A method of analysis of a sample by Raman spectrometry and discriminating fluorescence and elimination thereof in the analysis comprising, exciting the sample with a pulsed laser incident light wave for causing the sample to emit light, introducing the emitted light from the sample into a two-beam or a multiple-beam interferometer in which the round trip of the multiply reflected light is significantly longer than the duration of the incident light wave and shorter in duration than fluorescence from the sample, collecting the emitted light at the outlet of the interferometer, and spectrometrically analyzing the collected emitted light.

2. A method of analysis of a sample by Raman spectrometry and discriminating fluorescence and elimination thereof in the analysis according to claim 1, including prior to spectrometrically analyzing the emitted light introducing the emitted light collected at the outlet of the interferometer into a second multiple-beam interferometer having an optical path different from an optical path of the first-mentioned interferometer.

3. A method of analysis of a sample by Raman spectrometry and discriminating fluorescence and elimination thereof in the analysis according to claim 1, including varying the pulsed laser incident light wave to effect varying wave numbers.

4. A device for analysis of a sample by Raman spectrometry and discriminating fluorescence and elimination thereof in the analysis comprising, means for exciting the sample with a pulsed laser incident light wave for causing the sample to emit light, an interferometer for receiving the emitted light from the sample and collecting the light at an outlet thereof, and the interferometer having means for multiply reflecting light therein and for effecting a duration of the round trip of multiply reflected light significantly longer than the duration of a pulsed wave of the incident light and shorter in duration than fluorescence from the sample.

5. A device for analysis of a sample by Raman spectrometry and discriminating fluorescence and elimination thereof in the analysis according to claim 4, including a second interferometer for receiving the emitted light from the first-mentioned interferometer, and the second interferometer having an optical path length different than that of the first-mentioned interferometer.

6. A device for analysis of a sample by Raman spectrometry and discriminating fluorescence and elimination thereof in the analysis according to claim 4, in which the means for exciting the sample is a tunable laser for varying the incident light wave so that pulsed light waves of different wave numbers are applied to the sample.

7. A device for analysis of a sample by Raman spectrometry and discriminating fluorescence and elimination thereof in the analysis according to claim 4, including a spectral analyzer for analyzing light from said interferometer.

8. A device for analysis of a sample by Raman spectrometry and discriminating fluorescence and elimination thereof in the analysis according to claim 4, in which said interferometer is a Fabry-Perot interferometer.

9. A device for analysis of a sample by Raman spectrometry and discriminating fluorescence and elimination thereof in the analysis according to claim 4, in which said interferometer comprises a plurality of mirrors disposed with a certain shift to introduce the incident light wave without any loss.

10. A device for analysis of a sample by Raman spectrometry and discriminating fluorescence and elimination thereof in the analysis according to claim 4, including a microscope objective for receiving said emitted light for transmitting it to said interferometer, the interferometer having two offset mirrors multiply reflecting light therein, a second interferometer for receiving the light from said outlet of said interferometer, the second interferometer having mirrors for multiply reflecting the light received from the first-mentioned interferometer.

* * * * *